United States Patent
Anderson et al.

(10) Patent No.: US 7,380,940 B2
(45) Date of Patent: Jun. 3, 2008

(54) APPARATUS AND METHOD FOR ALLEVIATION OF SYMPTOMS BY APPLICATION OF TINTED LIGHT

(75) Inventors: John Douglas Anderson, Cambridge (GB); Ian Jordan, Ely (GB); Graham Stewart Brandon Street, Reading (GB); Shane William Thornton, Cambridge (GB)

(73) Assignee: Orthoscopics Limited, Reading (GB)

( * ) Notice: Subject to any disclaimer, the term of this patent is extended or adjusted under 35 U.S.C. 154(b) by 0 days.

(21) Appl. No.: 11/702,179

(22) Filed: Feb. 5, 2007

(65) Prior Publication Data

US 2007/0139611 A1    Jun. 21, 2007

Related U.S. Application Data

(60) Division of application No. 10/464,491, filed on Jun. 19, 2003, now abandoned, which is a continuation-in-part of application No. PCT/GB01/05544, filed on Dec. 17, 2001.

(30) Foreign Application Priority Data

Dec. 21, 2000 (GB) ................................. 0031384.1
Nov. 30, 2001 (GB) ................................. 0128705.1

(51) Int. Cl.
*A61B 3/10* (2006.01)
*A61B 3/00* (2006.01)

(52) U.S. Cl. ...................... 351/221; 351/200; 351/246

(58) Field of Classification Search ................ 351/200, 351/205, 221, 246, 44, 163, 177
See application file for complete search history.

(56) References Cited

U.S. PATENT DOCUMENTS 4,529,949 A     7/1985    de Wit et al.
4,648,051 A     3/1987    Wandell et al.
4,961,640 A    10/1990    Irlen
5,528,431 A     6/1996    Wilkins et al.
5,986,767 A    11/1999    Nakano et al.
6,459,425 B1   10/2002    Holub et al.
6,851,807 B2 *  2/2005    Holdeman .................. 351/203
6,870,523 B1    3/2005    Ben-David et al.
7,128,418 B2 * 10/2006    Sachtler ...................... 351/242
2004/0052076 A1  3/2004   Mueller et al.
2006/0109649 A1  5/2006   Ducharme et al.

FOREIGN PATENT DOCUMENTS

DE          199 01 669 A1    8/2000
WO          WO-02/049721 A1  6/2002

\* cited by examiner

*Primary Examiner*—Huy K Mai
(74) *Attorney, Agent, or Firm*—Birch, Stewart, Kolasch & Birch, LLP

(57) ABSTRACT

Apparatus and a corresponding method for the diagnosis and alleviation of symptoms of visually induced physiological defects and/or pathological conditions is provided. A plurality of narrow-band light sources are combined to constitute a color controllable lamp. A method for adjusting the settings of this lamp permits the optimum illumination for a particular subject to be found, whilst the latter carries out a task such as reading or writing. By use of the lamp to simulate the expected visual stimulus, to which the subject would be exposed if provided with viewing aids such as tinted spectacles and the like, an optimal selection from a database of such aids may be made or a new formulation defined. Inter alia, the symptoms of visual dyslexia, macular degeneration and visually induced migraine may be alleviated.

6 Claims, 8 Drawing Sheets

US 7,380,940 B2

APPARATUS AND METHOD FOR ALLEVIATION OF SYMPTOMS BY APPLICATION OF TINTED LIGHT

This application is a Divisional of co-pending application Ser. No. 10/464,491 filed on Jun. 19, 2003, and for which priority is claimed under 35 U.S.C. §120; which itself is a Continuation-in-Part of Application No. PCT/GB01/05544, filed on Dec. 17, 2001 under 35 U.S.C. §120 and which claims priority of Application No. GB 003/384 which was filed on Dec. 21, 2000 and GB 0128705 which was filed on Nov. 30, 2001 under 35 U.S.C. §119; the entire contents of all are hereby incorporated by reference.

The current invention is concerned with the provision or filtration of the illumination for a given task, such as reading or writing, and, specifically, with helping to alleviate the symptoms of certain physiological defects, such as dyslexia, or pathological conditions, such as migraine or macular degeneration, which may be suffered by the subject undertaking the task.

BACKGROUND

It is known that the response of the visual system is affected by the stimuli, which it receives. The threshold for such stimulation varies between individuals and, under adverse conditions, can significantly reduce performance. When the visual system is over stimulated, it reacts in a number of ways. Amongst a variety of undesirable effects, which can be caused, two examples include a drop in convergence sufficiency and a reduction in the ability to accommodate or fuse images. In addition, visual dyslexia may become apparent and migraines can be caused. Visual dyslexia is a condition of impaired reading and writing ability due to visual perception or visualisation problems. It is apparent therefore that for some it is necessary to modify the visual stimulus by changing the spectral distribution in a specific task e.g. reading and writing in school. In summary, it is well established that the colour of ambient lighting has a major influence on the effects of disorders such as dyslexia, epilepsy and migraine. In the case of dyslexia some sufferers can alleviate their reading problems by covering the page with a transparent coloured overlay in order to block out those wavelengths of light which give rise to an aspect of their problem. These overlays typically remove various amounts of simple primary colours, such as red, green or blue light and whilst they may assist with reading, they are of no value for writing.

In U.S. Pat. No. 5,855,428 (Wilkins) apparatus is described in which the spectral distribution of light from a fluorescent lamp to illuminate a surface to support reading material is altered by the interposition of specifically selected broadband filters. By adjustment of the position of the selected filter or filters different colours and saturation thereof can be selected.

In U.S. Patent Application No 2001/0005319 A1 (Ohishi et al.) an illumination control system, for general use, is described, in which the coordinates in colour space of the controlled illumination are arranged to follow a predetermined locus of points by mixing specific amounts of light from a plurality of differently coloured light emitting diodes (LED's).

Neither of these documents identifies the benefit of using sources which are characterised by providing light with a spectral distribution which is relatively narrow for application to the alleviation of the symptoms of the physiological defects and/or pathological conditions identified herein. This would be the case for laser sources, super-luminescent LED's and conventional coloured LED's, which provide light with a typical spectral bandwidth of between 17 nm to around 50 nm. The provision of illumination using additive light sources, such as LED's for the quantitative diagnosis and alleviation of the symptoms identified is the subject of this invention.

SUMMARY OF THE INVENTION

It is an object of the current invention to provide optimal illumination for a subject who may be suffering from physiological defects or pathological conditions of his/her visual system in order to alleviate the symptoms thereof.

It is a further object of the current invention to provide a means for specifying a colour formulation for the lenses of the spectacles to be worn by a patient suffering from one or more of the aforesaid physiological defects or pathological conditions.

Using a specific controllable light source for a particular task can be preferable to other forms of treatment (e.g. tinted spectacles), as the task lighting can be tailored precisely, for example to take account of the ambient conditions. A specific light is also of particular importance in certain eye conditions such as macular degeneration or cataract as optimum performance is directly related to visual stimulus input, particularly if the person has relatively poor vision. Specific stimulus modification will also be of great use in migraine prevention and treatment with possible uses in attention deficit hyperactivity syndrome and some types of epilepsy. Where it is desirable for the subject to use tinted spectacles, a controllable light source, as described herein, is a useful tool for defining the preferred filter characteristics of the tinted lenses.

Thus, according to one aspect of this invention means is provided for the quantitative diagnosis and/or alleviation of the symptoms of a plurality of visually induced physiological defects and/or pathological conditions suffered by a subject comprising a plurality of light sources, each of which is arranged to emit a respective spectral component of the visible spectrum, and control means for selecting a weighted mixture of said spectral components to provide illumination, characterised in that, in use, said illumination is arranged to illuminate a surface for viewing by the subject; said mixture is an additive combination of the spectral components emitted by at least two of said light sources; and the control means provides the means for varying the amount of illumination from each of said at least two light sources to impinge on said surface whereby, in use, a combination of said spectral components is provided to alleviate the symptoms of at least one of said visually induced physiological defects and/or pathological conditions.

The physiological defect may be visual dyslexia, visually induced migraine or macular degeneration.

Preferably a spectral component has a dominant wavelength which contributes to a respective first tristimulus value of the light entering an eye of the subject whilst substantially maximising the ratio of said contribution to said first tristimulus value to the root mean square of the contributions by said dominant wavelength to each of the second and third tristimulus values of the light entering the eye of the subject.

Advantageously, a first spectral component may comprise a dominant wavelength located between 465 nm and 475 nm. Another spectral component may comprise a dominant wavelength located between 520 nm and 530 nm. A third spectral component may have a dominant wavelength in the range 610 nm and 650 nm.

In preferred embodiments of the invention each light source comprises at least one light emitting diode arranged to provide one of the spectral components. Preferably a spectral component has a spectral power distribution having a width at half height which does not exceed 50 nm.

Advantageously, the illumination from each of the light sources is diffused prior to impinging on the viewed surface so that the relative intensity of the light impinging at two points spaced on said surface is substantially the same for each of said spectral components.

According to a further aspect of the invention means is provided for computing the combined effect of at least two of the active illumination spectra, the ambient illumination spectrum, the reflectance spectrum of the target or an illuminated surface, the transmission spectrum of at least one filter and the transmission spectrum of a surface coating over the visible spectrum, so that in use, the subject's retinal response may be predicted and the settings of the active light source and/or the formulation of a filter to be used by the subject may be optimised.

According to another aspect of the invention, a method for the diagnosis of a plurality of visually induced physiological defects and/or pathological conditions suffered by a subject comprises arranging a plurality of light sources to emit different spectral components within the visible spectrum, characterised by implementing the successive steps of:
 (a) assessing the subject's performance with a series of targets under different levels of each of a plurality of illuminants, comprising individual spectral components or pre-determined ratios thereof,
 (b) recording the optimum level (or at least the level at which the subject's performance improves) of each of said illuminants and
 (c) combining the levels of each respective illuminant as recorded in step (b) to provide a resultant additive mix of said illuminants.

Preferably, the method includes the further step of applying variations to the level of each of the spectral components in small steps whilst combined in order to establish the mix of said illuminants which substantially improves or optimises the subject's performance.

According to yet another aspect of the invention a method for simulating the performance of a selected filter comprises the steps of:
 (a) defining the tristimulus values of the tint which would be observed by a subject when said filter is used in transmission for viewing a reading surface (or other reflective or transmissive surface);
 (b) providing a colour controllable lamp comprising narrow band coloured light sources;
 (c) illuminating the reading surface (or other reflective or transmissive surface) for viewing by the subject with said lamp and
 (d) selecting the level of illumination provided by each light source so that, in use, the defined tristimulus values are observed by the subject.

Preferably the method includes the step of simulating a range of pre-formulated filters and lighting conditions, whereby the subject can select one or more filters for use under said conditions and the method includes the further step of formulating and/or selecting the filter to optimise the subject's performance.

The invention permits the formulation of filters with or without anti-reflection coatings for spectacles, contact lenses, coloured overlays or any other tinted material a purpose of which is to alleviate problems caused by colour related disorders of the human visual system.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

The present invention will become more fully understood from the detailed description given hereinbelow and the accompanying drawings, which are given by way of illustration only, and thus are not limitative of the present invention.

The invention will now be described with reference to FIGS. 1a to 7 in which:

FIG. 1a illustrates the response of the human visual system, as a function of the wavelength of the light incident thereon. Additional curves are provided to aid in the description of the invention.

FIG. 1b provides further curves showing the sensitivity characteristics of the colour receptors or cones at the human retina.

Figure 5:
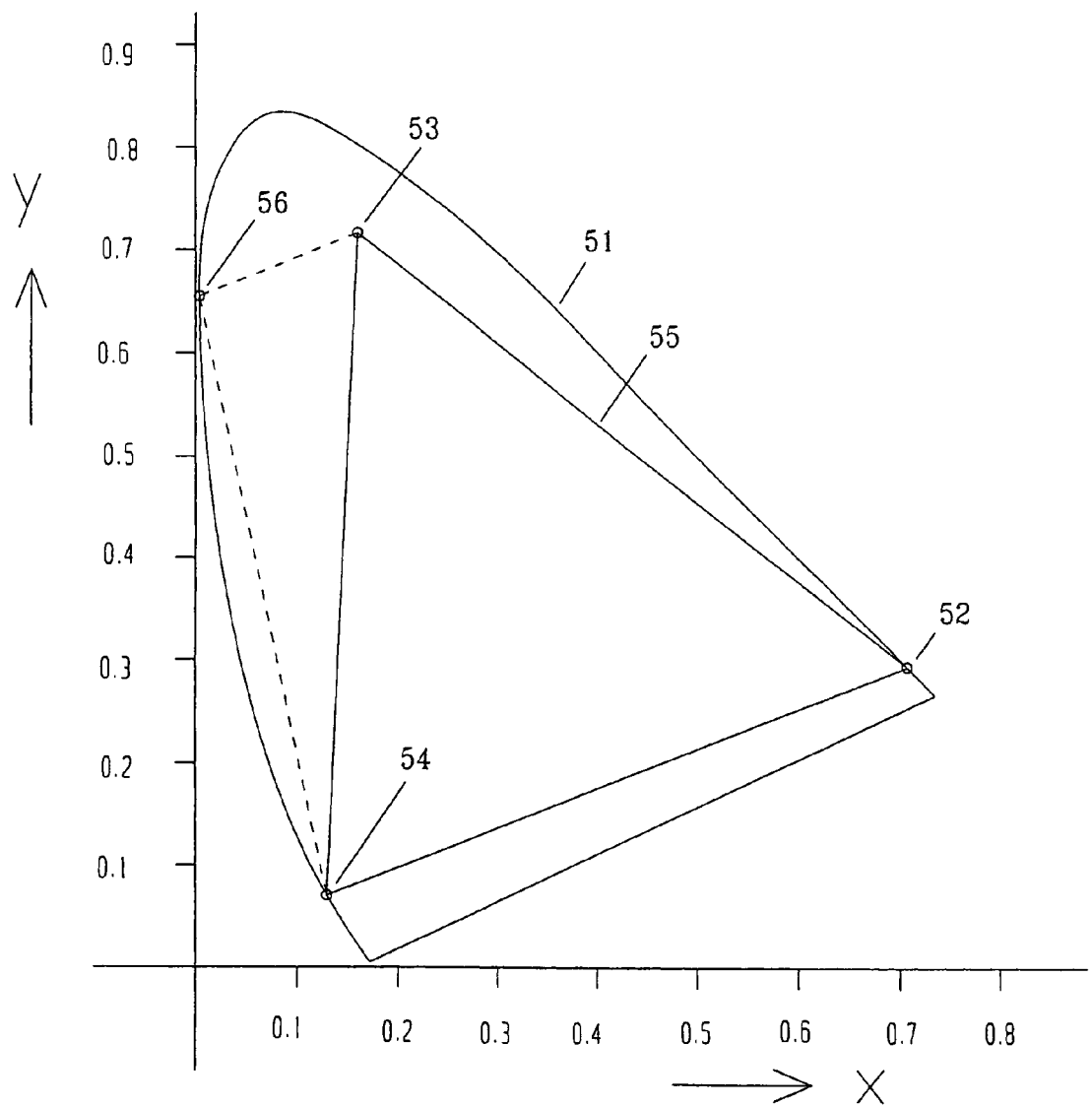

FIG. 5 provides a graphical illustration of colour space and the position of the colour co-ordinates of sources, as used in embodiments of the invention, within this.

Figure 6:
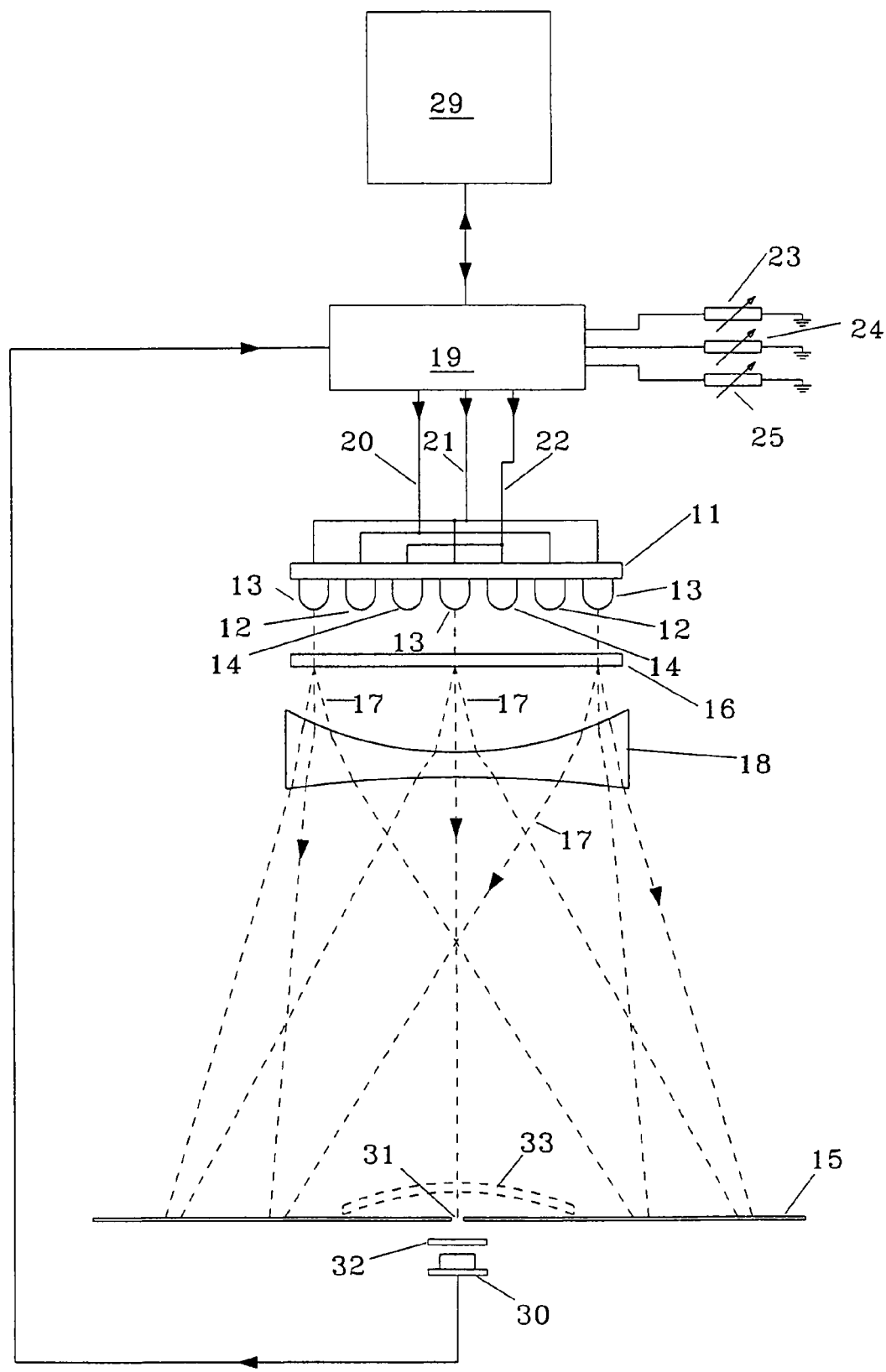

FIG. 6 illustrates an alternative embodiment of apparatus constructed in accordance with the invention.

Figure 7:
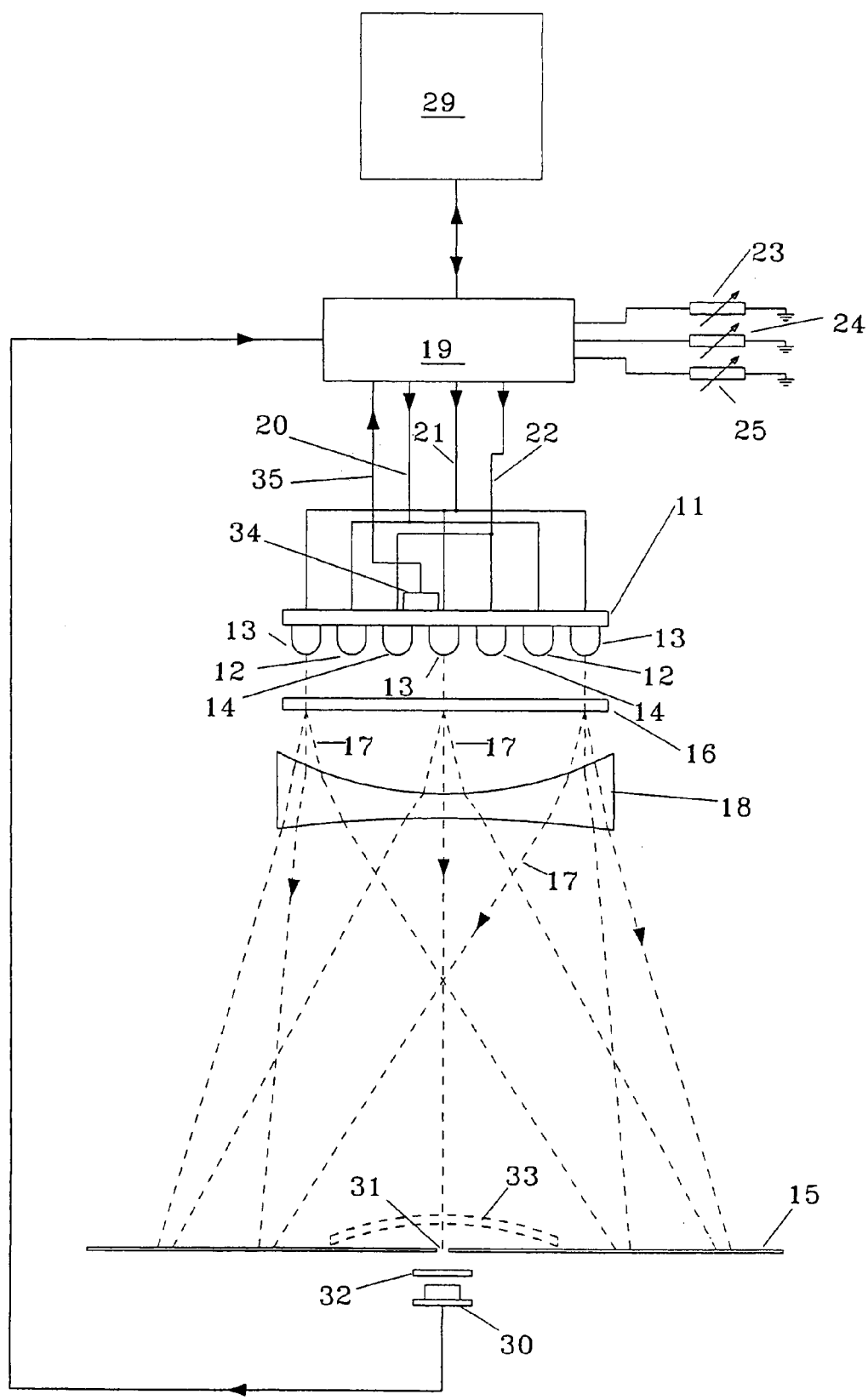

FIG. 7 illustrates a further embodiment of apparatus constructed in accordance with the invention.

Figure 1A:
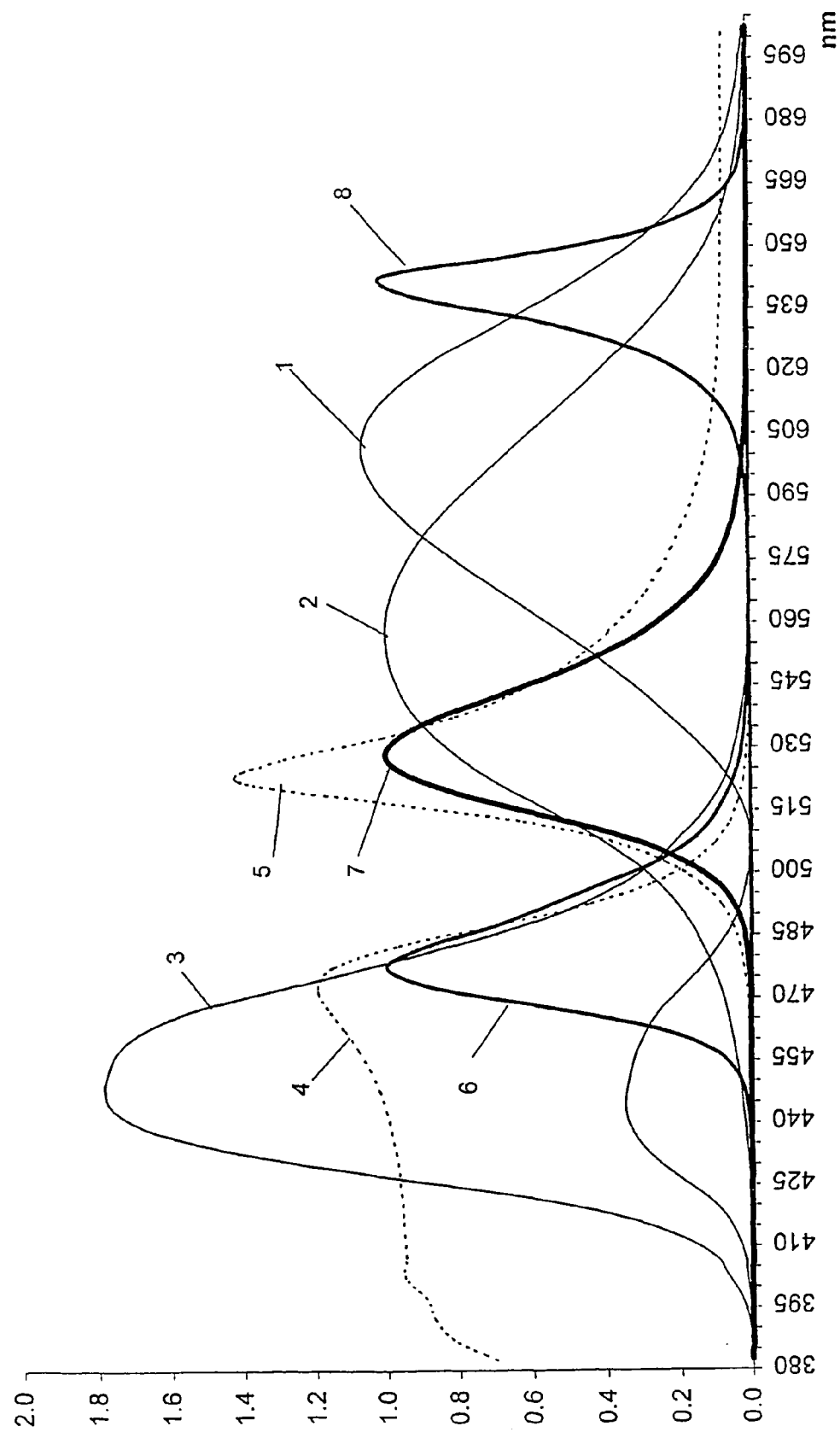
Figure 1B:
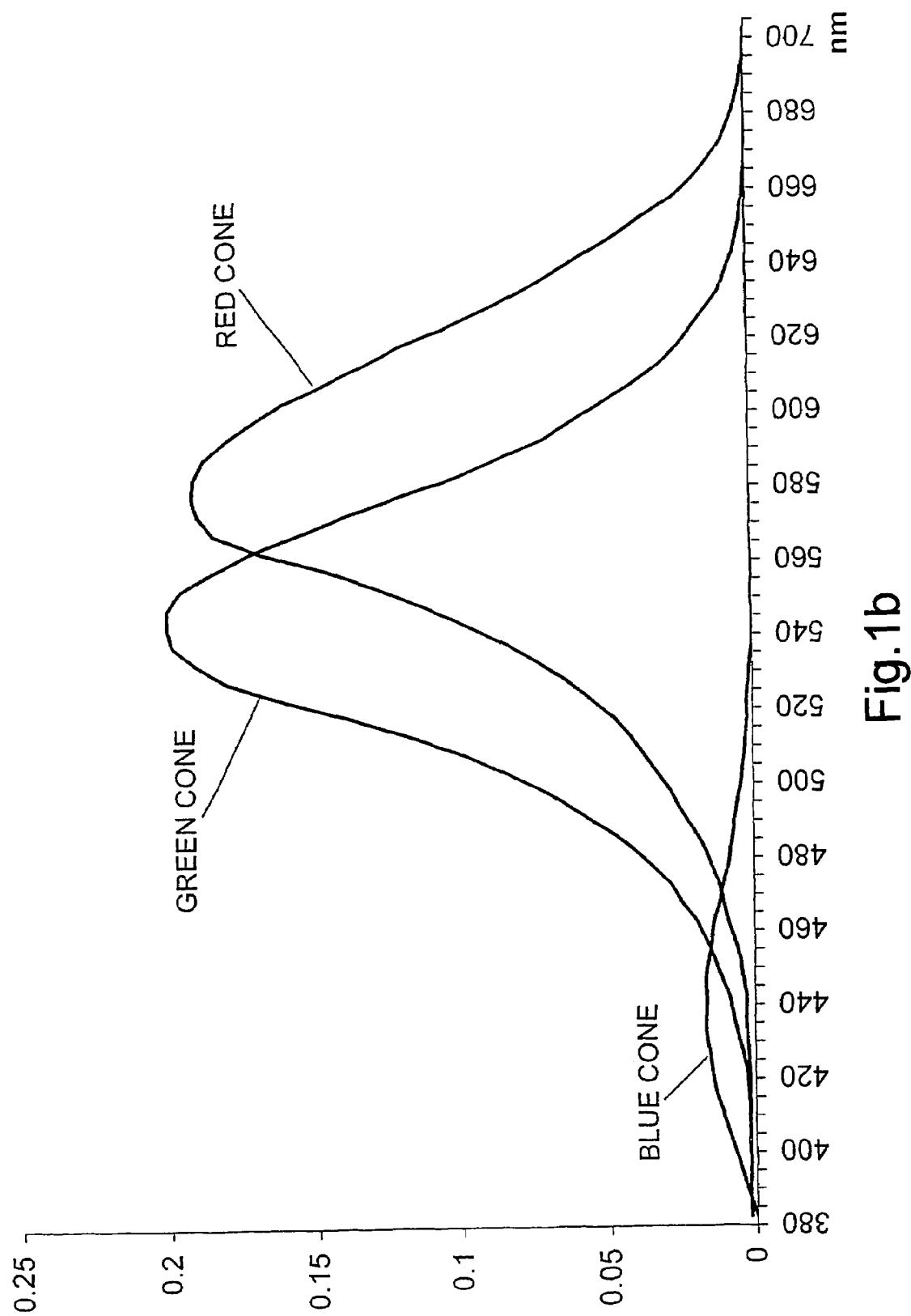

FIG. 1a shows the so-called spectral tristimulus values as a function of wavelength $\lambda$. These curves, which represent the amounts of idealised primaries required to match any of the pure spectral colours in the visible range and are related to the colour sensitivity characteristics of the human eye. Curve 1, typically designated as the function $\bar{x}(\lambda)$, primarily comprises the responsivity of the red sensitive cones of the human retina. The blue sensitive cones' responsivity is, suitably scaled, also included in this first tristimulus curve (see FIG. 1b). Curve 2 is, to a good approximation, a summation of the green and red cones' responsivity curves and is designated as the function $\bar{y}(\lambda)$ and actually corresponds to the overall spectral sensitivity of the eye. Curve 3 essentially comprises the blue cones' spectral sensitivity characteristic $\bar{z}(\lambda)$. It will be clear from these curves that the $\bar{x}(\lambda)$ curve has a subsidiary maximum in the blue region of the visible spectrum. A colour stimulus to the human visual system may be conveniently expressed as three values, the so-called tristimulus values (X, Y and Z), each of which involves an integral over the visible spectrum of the spectral power distribution reaching the retinal cones convolved with the respective tristimulus curve. For example:

$$X = \int_\lambda P(\lambda)\bar{x}(\lambda)\,d\lambda$$

Two further sets of curves are shown in FIG. 1a. One of these comprises dashed lines 4 and 5. Line 4 represents, following some normalisation, the ratio between $\bar{z}(\lambda)$ and the root mean squares of $\bar{x}(\lambda)$ and $\bar{y}(\lambda)$ and line 5 represents, on the same basis, the ratio between $\bar{y}(\lambda)$ and the root mean squares of $\bar{x}(\lambda)$ and $\bar{z}(\lambda)$.

The objective in calculating these merit functions is to find those points within the visible spectrum where the effect of the resultant stimulus of the human visual system is substantially expressed as a change to one of the tristimulus values, with the change to the other two being minimised relative thereto. What the two curves show is that, for a maximum change to Z relative to X and Y, stimulation of the human visual system at a wavelength of around 470 nm should be used and that, for maximum change of Y relative to X and Z, stimulation of the human visual system at a wavelength of around 520 nm is most effective. The purpose of the merit function is to find the optimal wavelength for maximising Y, relative to X and Z. Its value peaks near 520 nm, and drops to half its maximum at approximately 510 nm and also at 540 nm. A choice of wavelength within this range would be acceptable, though, for best results, a wavelength between 520 nm and 530 nm should be chosen. There is no clear choice for X, but a wavelength of around 640 nm is found to achieve good red saturation without too much loss of overall sensitivity.

It is an objective of this invention to provide a means for controlling the colour stimulation of the human visual system, so that an optimum ratio of X, Y and Z values can be established. When this is achieved, the visual or related disability and/or symptom of the subject, experienced under normal illumination, can be substantially alleviated. It will be clear that a combination of controllable narrow-band light sources, located respectively at substantially 470 nm, 520 nm and, say, 640 nm, will readily achieve this goal. All of these wavelengths are substantially achieved with commercially available LED's, the bandwidths of which typically vary from 17 nm to 47 nm. Typical examples of such emitted spectra are shown in FIG. 1a as curve 6, for Z, peaking at 470 nm (defined as blue herein), curve 7, for Y, peaking at 524 nm (defined as green herein) and curve 8, for X, peaking at around 640 nm in the red portion of the spectrum. The red wavelength is not as critical as the other two, for the reasons stated above.

By combining the light from the three different types of LED, as specified above, a wide range of colours can be achieved. A lamp comprising one or more of each type of LED, arranged in a variety of different ways, in which each group of a specific colour is controlled by an adjustable signal, can be used to optimise the illumination for a given subject carrying out a specific task, such as reading or writing. For example, a person who suffers from dyslexia may have a reading difficulty significantly alleviated by the partial or complete exclusion of the red illumination, in effect, by reducing the stimulation of the red sensitive cones.

Embodiments of the current invention use a multi-colour light emitting diode (LED) array, operated within an optical assembly so that colours can be mixed to create the optimum lighting for any patient. An array of different coloured LEDs, typically red, green and blue, in accordance with the principles outlined above are operated either individually or together, so that it is possible to select single primary colours or combine the various LEDs to give different hues and illuminance. The primary advantage with this type of lighting being that it can be used for both reading and writing.

In practice, each LED type (red green or blue) has its own chromaticity co-ordinates and the differences between that of one type and of the other two determine the range of colours that can be achieved by appropriately combining their outputs.

The table below sets out typical values of x, y and z (in which z is defined as 1−x−y) for each of the three LED types

|  | x | y | z |
| --- | --- | --- | --- |
| Red | 0.706 | 0.294 | 0.000 |
| Green | 0.159 | 0.717 | 0.124 |
| Blue | 0.129 | 0.071 | 0.800 |

A method, well established in the prior art, for depicting a particular colour within a continuum of possibilities is to represent this as a point on a chromaticity diagram of x against y. In such a diagram (see FIG. 5, which depicts the CIE 1931 chromaticity diagram), all possible colours fall within a defined and closed locus of points 51. In $$\begin{bmatrix} \text{Red\_demand} \\ \text{Green\_demand} \\ \text{Blue\_demand} \end{bmatrix} = \begin{bmatrix} 1.095 & -0.215 & -0.158 \\ -0.634 & 1.543 & -0.033 \\ 0.063 & -0.151 & 0.796 \end{bmatrix} \times \begin{bmatrix} x \\ y \\ z \end{bmatrix}$$

the colour co-ordinates 52, 53 and 54 of each of the three types of LED, between them, define a triangle 55 within this complete colour space. The larger this triangle, the greater the range of colours which can be produced by varying the contributions to the illuminant from each of the LED types. For each target value of x and y, there will be a defined output requirement from each type of LED. It may be shown that, after inverting the matrix comprised of the three colour co-ordinates (each having three terms) of the red, green and blue LED's provided above and after applying suitable compensation factors to each drive of the LED types, amongst other things, to compensate for their spectral distributions and quantum efficiencies, a 3×3 matrix may be constructed, which defines the required demand to apply to each of the primary sources in order to obtain a specific point (x, y, z) in colour space. This matrix is of the general form and is used as follows:

What the above three relationships define is that, in this particular example and for a target white illuminant (x=0.333, y=0.333, z=0.333) to be provided, relative demands of 0.241 from the red source, 0.289 from the green source and 0.236 from the blue source are required. If the chromaticity co-ordinates of the red source (0.706, 0.294, 0) are applied to the right hand side of the above equality then, as expected, the only demand required is that of the red source. The three LED types 12, 13 and 14 have chromaticity co-ordinates, depicted in FIG. 5 as points 52, 53 and 54. As stated above, theses define a triangle 55 within the closed locus of points 51 in the chromaticity diagram which represents the continuum of all colours. If chromaticity co-ordinates which fall outside this triangle are applied to the right hand side of the above equality, a negative demand from at least one of the primary sources would be indicated. This is not possible and consequently the triangle defines those colours which the colour selectable lamp of this invention can typically provide. It is possible, within the scope of this invention, to introduce additional narrowband light sources, such as, for example, a narrow band source having its peak at 505 nM and having colour co-ordinates (x, y, z) of (0.004, 0.655, 0.341). This is shown as point 56 in FIG. 5. By defining a second matrix, we may calculate the demands required from the original green and blue sources together with that from this new blue-green source, in order to access that portion of colour space bounded by the triangle defined by points 53, 54 and 56.

In practice the narrow-band sources used in preferred embodiments of this invention and their particular position in colour space provide a very large gamut of possible colours. A colour selectable lamp constructed in accordance with this invention allows much greater flexibility than that of systems which employ subtractive broadband filters to control the colour of the illuminant and provides the opportunity to better taylor the illuminant to each user. This could have important applications in the office and school environment where ambient lighting limitations contribute to reading and writing problems for some individuals.

Figure 2:
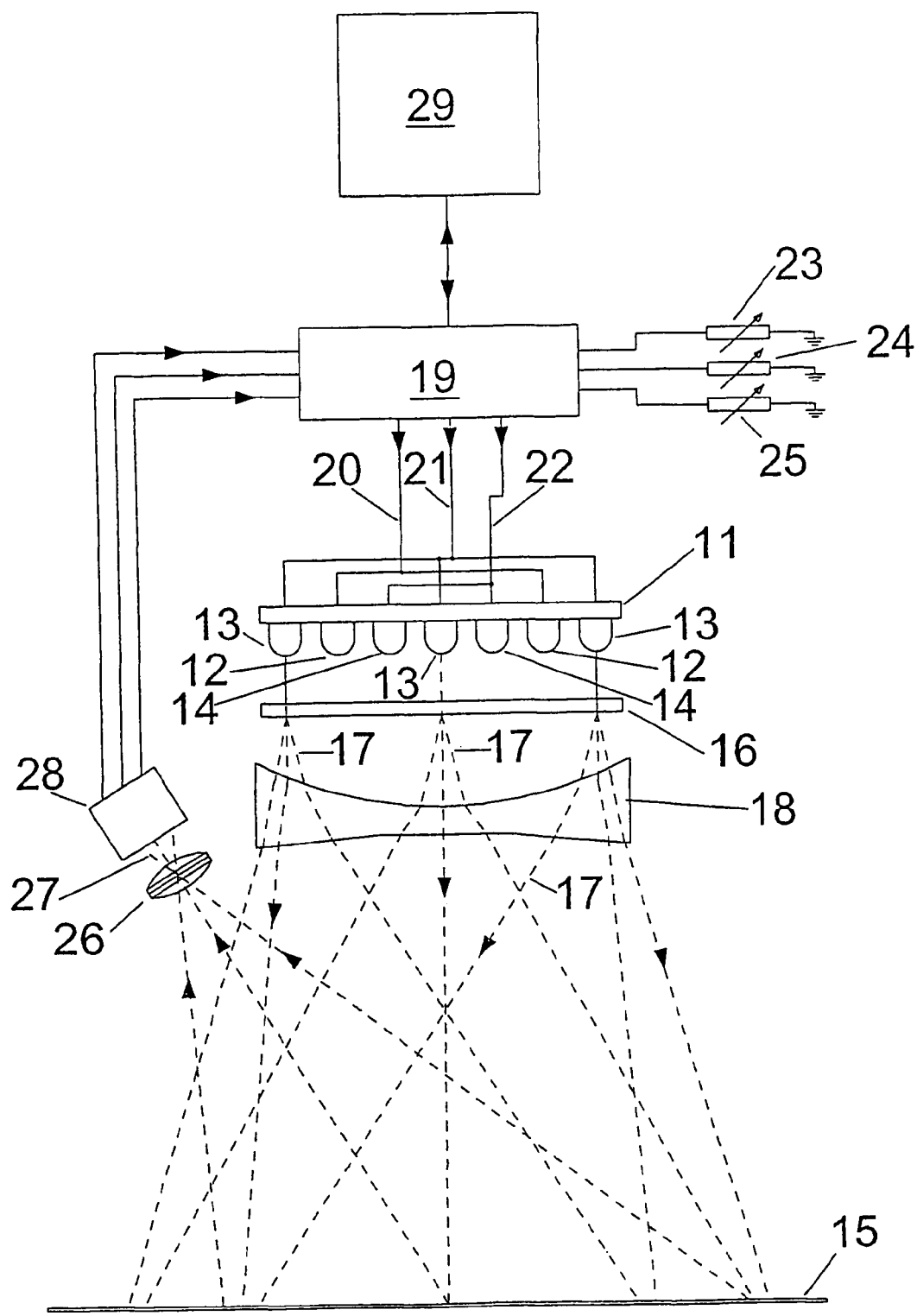
FIG. 2 illustrates, diagrammatically, apparatus constructed in accordance with the invention in order to provide a colour controllable source of illumination.

Turning to FIG. 2, this shows diagrammatically how a number of components may be combined in accordance with the principles of the invention to form a colour controllable light source.

A lamp 11 comprises an array of LED's. The array includes red emitters 12, having an emission spectrum peaking at 640 nm, green emitters 13, having an emission spectrum peaking at 524 nm, and blue emitters 14, having an emission spectrum peaking at 470 nm. The LED's are distributed in such a manner that the field illuminated by each type at a reading surface 15 is approximately the same. In order to ensure that there are no substantial differences in the mix of colours at any given point on the reading surface, a diffuser 16 is placed in the path of the emitted light. This diffuser may take several different forms. A lenticular screen or microlens array is found to be effective, as well as other kinds of efficient light scattering media. For example, a material comprising changes of refractive index over short distances can be very effective.

The effect of distributing the individual LED's in an even manner, together with the action of the diffuser 16, is to provide a very even mix of light at the reading surface 15. In order to extend the effective area of illumination, a divergent lens assembly 18 can be very useful. Although this is shown as a conventional meniscus lens, a compact equivalent, such as a fresnel lens may also be used.

A control unit, typically a microprocessor, 19 receives a number of different inputs, prior to driving each group of LED's via outputs 20 for blue, 21 for green and 22 for red. At its simplest level, variable resistors 23, 24 and 25 are used to set the light output from the red, green and blue LED's respectively. The components identified, thus far, comprise a colour controllable lamp. This can be used by a subject to select a particular combination of red, green and blue illuminants, which is optimal for his or her reading or writing performance.

In practice, a more sophisticated version of such a lamp would adapt the light output demanded from the LED array to take account of the ambient conditions. In FIG. 2 a lens 26 forms an image on the receiving surface 27 of a camera 28. This may be a CCD or other photo-detector array, behind a colour filter array. Using known principles, the video signal from the CCD can be analysed to provide a reading of the level of illumination at surface 15, in addition to its colour mix. There will be a specific matrix, which will allow the measure of light passing through each component of the camera's colour filter array to be translated into a red, green and blue LED light combination. Some of this will be contributed by the ambient light impinging on surface 15. The output, required from each type of LED, is adjusted by control unit 19, accordingly. As a consequence of the use of camera 28 to monitor the illumination of surface 15 the resulting system will also be stabilised against other variations, such as changes in the efficiency of the optics or LED's.

The apparatus of FIG. 2 can be very useful as a diagnostic tool, particularly when used in conjunction with a computer, shown as block 29. Amongst other things, the computer can be used to store the selected tint of the illumination at surface 15, when this has been optimised or at least substantially improved for the subject.

Figure 3:
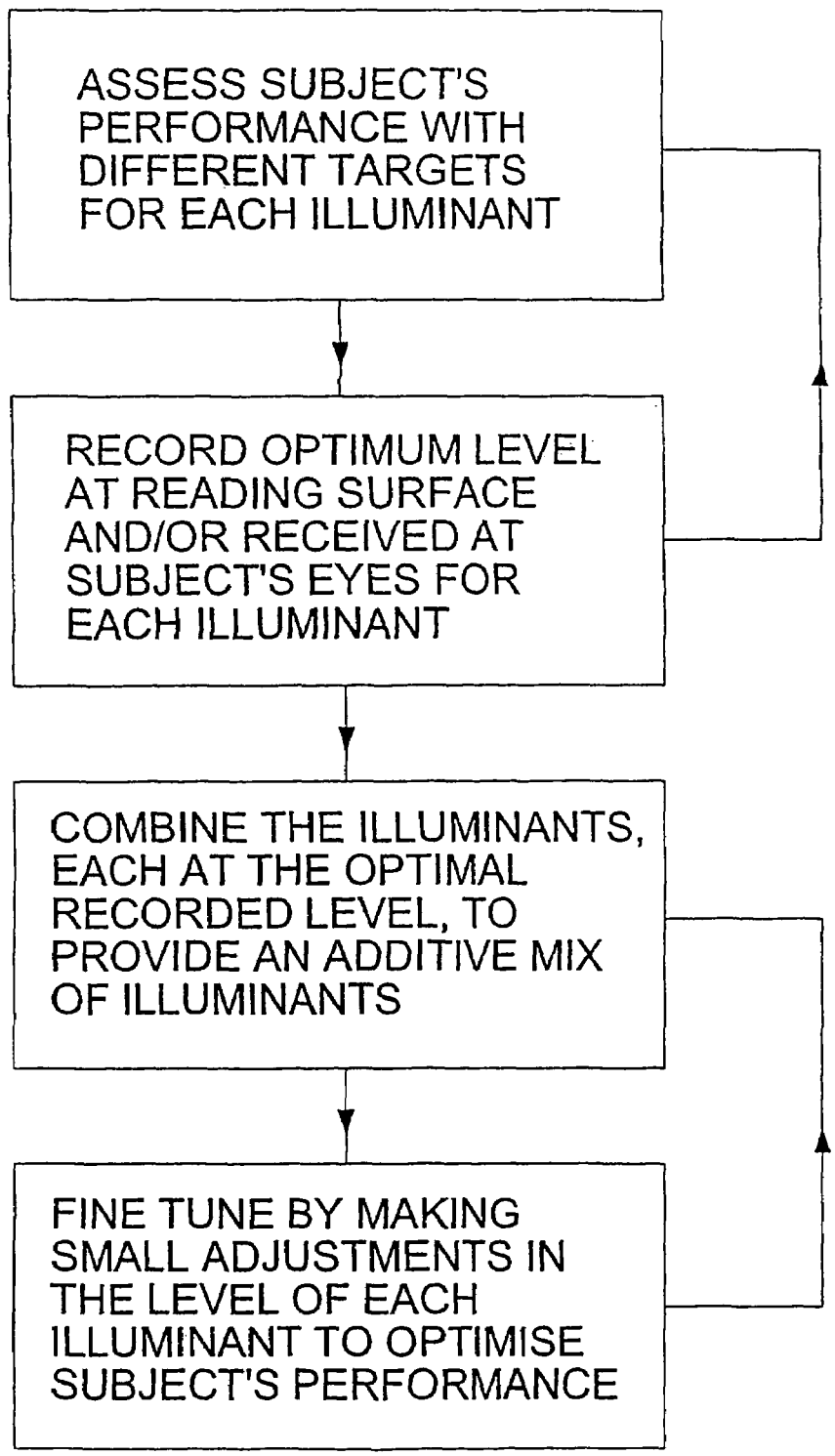
FIG. 3 shows in flowchart form a preferred method in accordance with the invention for use of the apparatus of FIG. 2.

Turning to FIG. 3, this outlines, in summary form, a methodology in accordance with the invention for establishing the optimal illumination for a specific subject, such as, for example, a person suffering from visual dyslexia.

The first step in the procedure is to determine the best illumination conditions for a variety of different reading tests. This is done by illuminating the reading material at surface 15 of FIG. 2 with one of the illuminants. This is increased in brightness, until the subject is satisfied that the optimal brightness has been found. It may be necessary to pass through the optimum and to reduce the brightness slightly to establish that setting. This step is repeated for each of the illuminants (LED groups), separately. It is quite possible that the optimum level for the red illumination may be at 50% of maximum, for a particular subject, whereas the green and blue illuminants would be quite acceptable at their maximum levels. The particular settings for each illuminant will be highly subject dependent. Step 2 is to record the optimum level (or the level at which the subject's performance improves) for each illuminant, either directly from the controls or transferred automatically to a computer.

Once the individual optima have been established, the recorded levels of each primary illuminant are combined in Step 3 of the procedure. Step 4 is to fine tune this mixture by making small adjustments to each primary (red, green and blue), in small steps, until an optimum or at least improved mix is established for the subject. The step changes would be made in both directions, decreasing or increasing the particular illuminant, and establishing whether there is an improvement or otherwise in the subject's performance. By iteration of Steps 3 and 4, the best combination is found.

One of the key objectives of this invention is to use the arrangement of FIG. 2 as a diagnostic tool, in order to arrive at an improved or even optimal formulation for the filters to be provided for the lenses of spectacles or contact lenses to be worn by the subject. The colour of the light reaching the subject's eyes is recorded by the system of FIG. 2 and stored in computer 29. This record will typically contain information about the settings of the LED sources and, if any, the colour and level of the ambient illumination at the time that the measurements were made. By prior knowledge or use of colour camera 28, any colouration of the reading surface 15 may also be accommodated.

Figure 4:
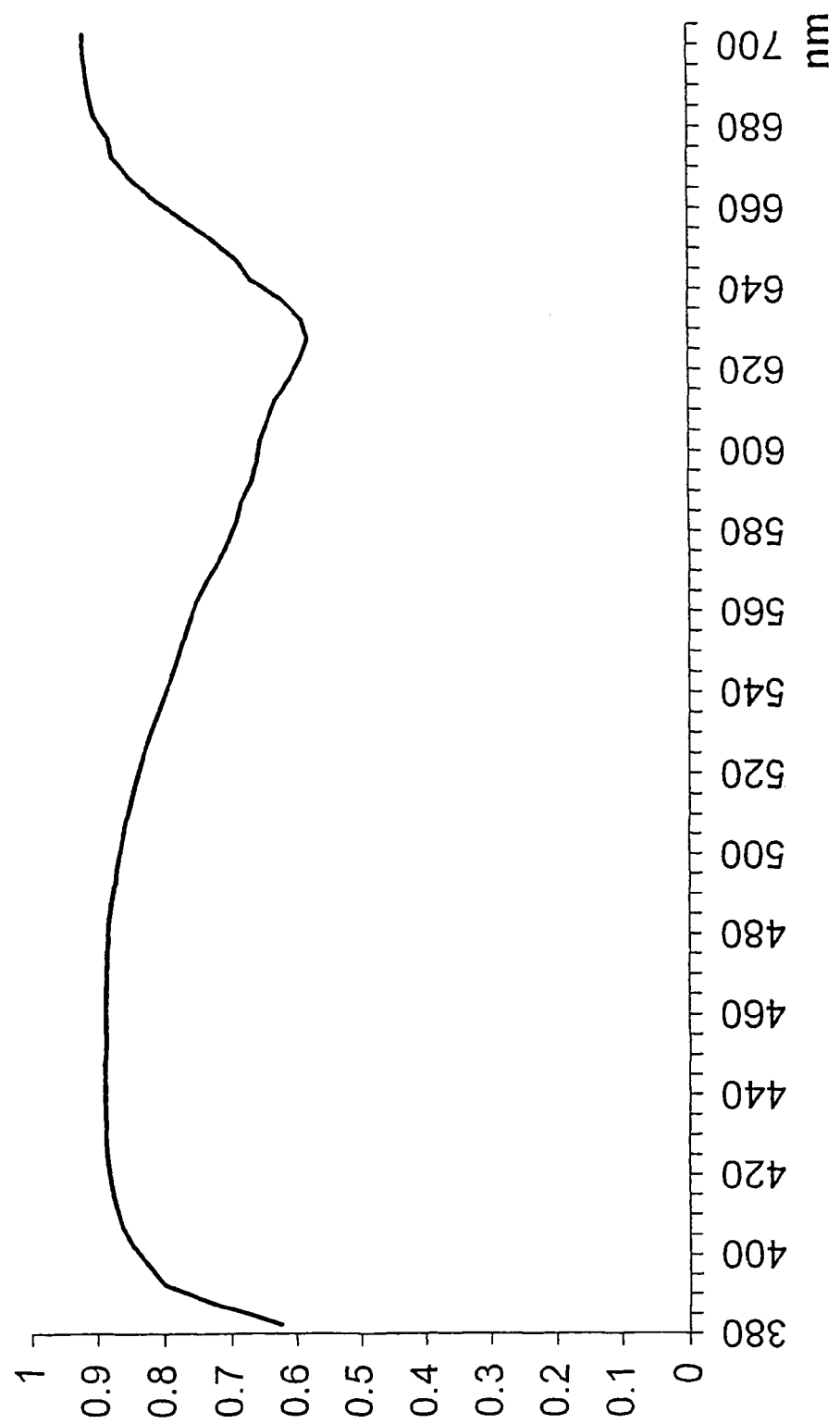
FIG. 4 shows the transmission spectrum of a typically tinted lens, formulated to reduce the relative stimulus to one type of cone, in accordance with the invention.

In practice there will be a finite selection of filter formulations available. A typical filter characteristic is shown in FIG. 4. Curve 41 represents the percentage transmission of a red absorbing (blue tinted) filter as a function $T(\lambda)$ of the wavelength $\lambda$ of the light incident upon it. Our interest is in knowing what the response at the retina of each eye will be for each of the cones when the subject views material through this filter. In order to calculate this we must multiply each of the tristimulus curves at every wavelength with the spectral distribution of the light arriving at the retina and integrate this result over the visible spectrum. The result will be one of the tristimulus values for the particular tint, as defined by the CIE 1931 chromaticity diagram (as shown in FIG. 5). It will comprise a number of components, including the following:

1) the spectrum of the illumination which the subject will use when reading or writing (This could be daylight or light from a tungsten or fluorescent lamp and each will have a different spectrum),
2) the background reflectance spectrum of the material being read and
3) the relevant tristimulus curve.

For the response corresponding to each of the tristimulus values the integral required will be of the form $$X = \int_{380nm}^{780nm} I(\lambda)T(\lambda)R(\lambda)\bar{x}(\lambda)\,d\lambda,$$

Where $I(\lambda)$ is the illumination spectrum, $T(\lambda)$ is the filter's transmission spectrum, $R(\lambda)$ is the illuminated substrate's reflectance spectrum and $\bar{x}(\lambda)$ is the relevant tristimulus curve, shown, suitably normalised as curve 1 in FIG. 1a. Two further integrals would be calculated for the Y and Z tristimulus values.

It will be clear to those versed in the art that the same tristimulus values can be achieved with a different illumination spectrum and, in principle, without the use of the intervening transmission filter. Indeed, where the illumination spectrum is comprised of the combination of the three primary illuminants provided by the red, green and blue LED's of FIG. 2, this spectrum will have three well-defined peaks. As already explained, by reference to FIG. 1a and FIG. 1b, each of these peaks will have a particularly significant influence on only one of the tristimulus values.

It is a further objective of this invention to simulate the effect of any particular filter by providing illumination which simulates the effect on the visual system that would result from the use of that filter under the expected lighting conditions. Thus the LED outputs, with the reflectance characteristics of the reading surface 15 in FIG. 2 being taken into account, must be adjusted to simulate that part of the function under the integral above represented by $I(\lambda)T(\lambda)R(\lambda)$. In effect, $I(\lambda)T(\lambda)$ will be replaced by the following expression:

$$E(\lambda)=rR(\lambda)+gG(\lambda)+bB(\lambda),$$

where r, g and b represent the components of each of the primary illuminants and $R(\lambda)$, $G(\lambda)$ and $B(\lambda)$ are the respective spectral power distributions of these, as shown in FIG. 1a as curves 8, 7 and 6 respectively.

For every choice of filter characteristic available there will be values of r, g and b which will simulate the effect for the subject under a particular selection of lighting. Having established an optimal tristimulus value for the subject by using the procedure of FIG. 3, a best choice of tint may be selected or formulated. A database of all standard filters may be held on computer 29, in order to provide a convenient method for prescribing an available choice of filter. The precise effect of that filter being available for the subject to experience by simulation using the apparatus of FIG. 2

It follows from this that the apparatus of FIG. 2 may be used to determine the relative colour response of an individual's eye. In this case a surface of known colour reflectance is made to look white by adjusting r, g and b values above. The expression describing this is:

$$CC[\text{surface}(\lambda)*(E_r(\lambda)*rR(\lambda)+E_g(\lambda)*gG(\lambda)+E_b(\lambda)*bB(\lambda))]=CC_p$$

where $CC[f(\lambda)]$ is the colour co-ordinate transformation of a spectrum, $CC_p$ is the perceived white colour response and $E_r(\lambda)$, $E_g(\lambda)$ and $E_b(\lambda)$ are the eye responses. For a known surface and instrument settings and a normal eye response then the perceived white colour will correspond with the actual colour co-ordinates of white with $CC_p=[0.33,0.33,0.33]$.

For an eye with a different colour response $CC_p$ will be at a different position in colour space and the vector between this position and nominal white will be a measurement of relative colour response of the eye.

By further reference to FIG. 1a it also follows that, in order to reduce the X tristimulus value to a minimum, a light source with its energy concentrated at around 505 nm is required. Such a facility may prove particularly useful in circumstances where the function of the lamp is a diagnostic one and a complete absence of the X stimulus is desired. Its provision, as illustrated earlier herein, will also increase the range of tints which can be simulated by apparatus constructed in accordance with the invention.

Although the embodiment of FIG. 2 incorporates a divergent lens to spread the illumination over the desired area, this is not an essential component for the operation of the lamp, as the combination of a diffuser and suitably positioned LED's can be chosen to illuminate any specific area. Whilst the embodiments illustrated herein utilise LED's with relatively narrow-band emission spectra, other devices such as laser sources may be used as alternative illuminants. Furthermore, whereas a camera 28 is employed to analyse the colour of the illumination of surface 15, this could, in practice, be replaced by a series of photodiodes receiving light from this surface through suitable colour filters.

An alternative embodiment of the invention is illustrated in FIG. 5. This is similar to the embodiment of FIG. 2, but, instead of a CCD camera to view the light scattered from reading surface 15, a photocell 30, having precisely known spectral sensitivity, is positioned behind a small aperture 31 in surface 15 at which material to be viewed under a colour controlled illuminant would, in normal use, be placed. A diffuser 32 is placed immediately in front of photocell 30 to ensure that it responds uniformly to light from lamp 11, regardless of its point of origin at the lamp. Another optical arrangement to achieve this end result would comprise a lens (not shown) positioned between aperture 31 and photocell 30 and arranged to image the lamp onto the photosensitive area of photocell 30. The function of photocell 30 is twofold. It is used within an automated calibration procedure to adjust the respective drive currents to the red 12, green 13 and blue 14 LED's, in order to provide the correct balance for a white illuminant. Each LED type is activated in sequence and the power adjusted to ensure that the expected response, which can be calculated from the known spectral output of the LED and the corresponding spectral sensitivity of photocell 30, is received by the latter. Once the LED's have been balanced in this way, they may be used in conjunction with photocell 30 to test the transmission characteristic at three points of the spectrum of any lens (shown in broken line format as item 33 in FIG. 5) which has been formulated using a known filter material. For a given filter material the ratios of the three responses will be known and the density of the filter will be calculable. The combination of the selectable LED's and known photocell characteristic, enables a precise validation of transmission characteristics of lens 33 to be carried out.

An embodiment of the invention which includes temperature compensation to improve precision is illustrated in FIG. 7. A temperature sensor 34 is included and is attached to the assembly of lamp 11, which incorporates the LED's. The temperature of this assembly is relayed via line 35 to microprocessor 19. It has been established that the quantum efficiency of an LED typically changes as a function of its operating temperature and some loss of light output may be expected as the device's temperature increases. This effect can be effectively offset by adjusting the demand to the LED as a function of temperature and line 35 provides microprocessor 19 with the necessary means for doing so.

It will be clear to those skilled in the art that the manufacture of any tinted lens, which is formulated as a result of a prescription derived from the simulation of such lens using apparatus and method constructed in accordance with the teachings of this invention, is the intended end product of such simulation and thereby falls within the scope of the invention.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

The invention claimed is:

1. A method for the simulation of the use of a filter under expected lighting conditions comprising:
    defining the tristimulus values of a tint which would be observed under the expected lighting conditions by a subject when said filter is used in transmission for viewing a surface,
    providing a colour controllable lamp including narrow-band coloured light sources,
    selecting the level of illumination provided by each light source and
    controlling the colour controllable lamp to illuminate the surface for viewing by the subject so that, in use, the defined tristimulus values are observed by the subject.

2. The method of claim 1 further comprising the step of simulating a range of pre-formulated filters and lighting conditions, whereby the subject can select one or more of said pre-formulated filters for use under said lighting conditions.

3. The method of claim 1 which includes the further step of formulating and/or selecting the filter to improve the subject's performance.

4. The method of claim 2 which includes the further step of formulating and/or selecting one of said preformulated filters to improve the subject's performance.

5. A method as claimed in claim 1 applied to the formulation of any one of filters and anti-reflection coatings for spectacles, contact lenses, coloured overlays and any other tinted material through which the subject may view the surface a purpose of which is to alleviate problems caused by colour-related disorders of the human visual system.

6. An article formulated by the method of claim 5.

* * * * *